US00PP28005P2

(12) United States Plant Patent
Probst

(10) Patent No.: US PP28,005 P2
(45) Date of Patent: May 9, 2017

(54) ***COREOPSIS* PLANT NAMED 'STARLIGHT'**

(50) Latin Name: ***Coreopsis* hybrid**
Varietal Denomination: Starlight

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 94 days.

(21) Appl. No.: 14/545,040

(22) Filed: Mar. 19, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

American Nurseryman 2015 Dec. 2014, retrieved on Aug. 4, 2016, retrieved from the Internet at <http://www.amerinursery.com/content/AN/pdf/2015_AN_NewPlants.pdf> pp. 4 and 36.*

Emerald Coast Grower Starter Plants 2014-2015 catalog, pp. 1-3, 8-9 and 26-27.*

Pioneer Gardens, Inc. 2014-2015 Program and Availability, retrieved on Aug. 18, 2016, retrieved from the Internet at <https://nebula.wsimg.com/a8e14aaf5f2c1ab73574f0980ec0bb03?AccessKeyId=D4DC3ED90C9EAD58C2B4&disposition=0&alloworigin=1> Aug. 27, 2014, pp. 1-20.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Starlight' that is characterized by its compact plant habit, its nearly sterile florets result in a floriferous and long bloom season that does not require deadheading with bloom commencing in mid-June and lasting until hard frost in Connecticut, its large star-shaped inflorescences with ray florets that are cream-white in color with a purple streak at the base that expands to cover almost the entire surface of the ray florets in cooler temperatures, its cold hardiness at least to U.S.D.A. Zone 5a, and its resistance to powdery mildew and leaf spot.

2 Drawing Sheets

Botanical classification: *Coreopsis* hybrid.
Variety denomination: 'Starlight'.

BACKGROUND OF THE INVENTION

The present invention relates to a new and distinct cultivar of *Coreopsis* plant, botanically of hybrid origin and known as *Coreopsis* 'Starlight' and will be referred to hereinafter by its cultivar name, 'Starlight'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars in a wide range of flower colors and plant forms that have sturdy plant habits, exhibit a true perennial habit, and are cold hardy to at least U.S.D.A Zone 5a.

The new cultivar arose from a cross made by the Inventor in August of 2010 in his test garden in Hubbardston, Mass. between an unnamed, proprietary plant in the Inventor's breeding program, reference no. Q1 09-5 (not patented), as the female parent and and pollen that was pooled from a variety of unnamed, proprietary plants (not patented) from his breeding program as the male parent (all nearly sterile). The exact male parentage is therefore unknown. 'Starlight' was selected in September 2011 as a single unique plant amongst the resulting seedlings.

Asexual propagation of the new cultivar was first accomplished by stem cuttings under the direction of the Inventor in Kensington, Conn. in September of 2011. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Starlight' as a new and distinct cultivar of *Coreopsis*.

1. 'Starlight' exhibits a compact plant habit reaching an average of 25 cm in height and 50 cm in width.
2. 'Starlight' is nearly sterile and exhibits a floriferous and long bloom season that does not require deadheading, blooming commences in mid-June and lasts until hard frost in Kensington, Conn.
3. 'Starlight' exhibits large star-shaped inflorescences with ray florets that are creamy white in color with a purple streak at the base that expands to cover almost the entire surface of the ray florets in cooler temperatures.
4. 'Starlight' exhibits cold hardiness at least to U.S.D.A. Zone 5a.

5. 'Starlight' exhibits resistance to powdery mildew and leafspot.

The female parent of 'Starlight' differs from 'Starlight' in having inflorescences with ray florets that are white in color with a very small purple-colored eye, in having a taller plant height, and in being fertile. 'Starlight' can be most closely compared to the *Coreopsis* cultivars 'Star Cluster' (U.S. Plant Pat. No. 23,035) and 'Snowberry' (U.S. Plant Pat. No. 18,560). 'Star Cluster' is similar to 'Starlight' in being resistant to powdery mildew and leaf spot, in having flowers that are white in color with purple at the base, and in having a long bloom season that does not require deadheading. 'Star Cluster' differs from 'Starlight' in being taller in height and in having inflorescences that are slightly smaller in size and more rounded in shape with ray florets that have a small purple blotch at the base rather than a streak. 'Snowberry' is similar to 'Starlight' in having inflorescences with ray florets that are whitish in color. 'Snowberry' differs from 'Starlight' in having flowers that are much smaller in size and in having a taller plant height.

BRIEF DESCRIPTION OF THE DRAWINGS

The accompanying colored photographs illustrate the overall appearance and distinct characteristics of the new *Coreopsis*. The photographs were taken of a three month-old plant (from a 128-cell plug) of 'Starlight' as grown outdoors in a one-gallon container in Kensington, Conn.

The photograph in FIG. 1 provides a view of 'Starlight' in bloom in warm temperatures.

Figure 1:
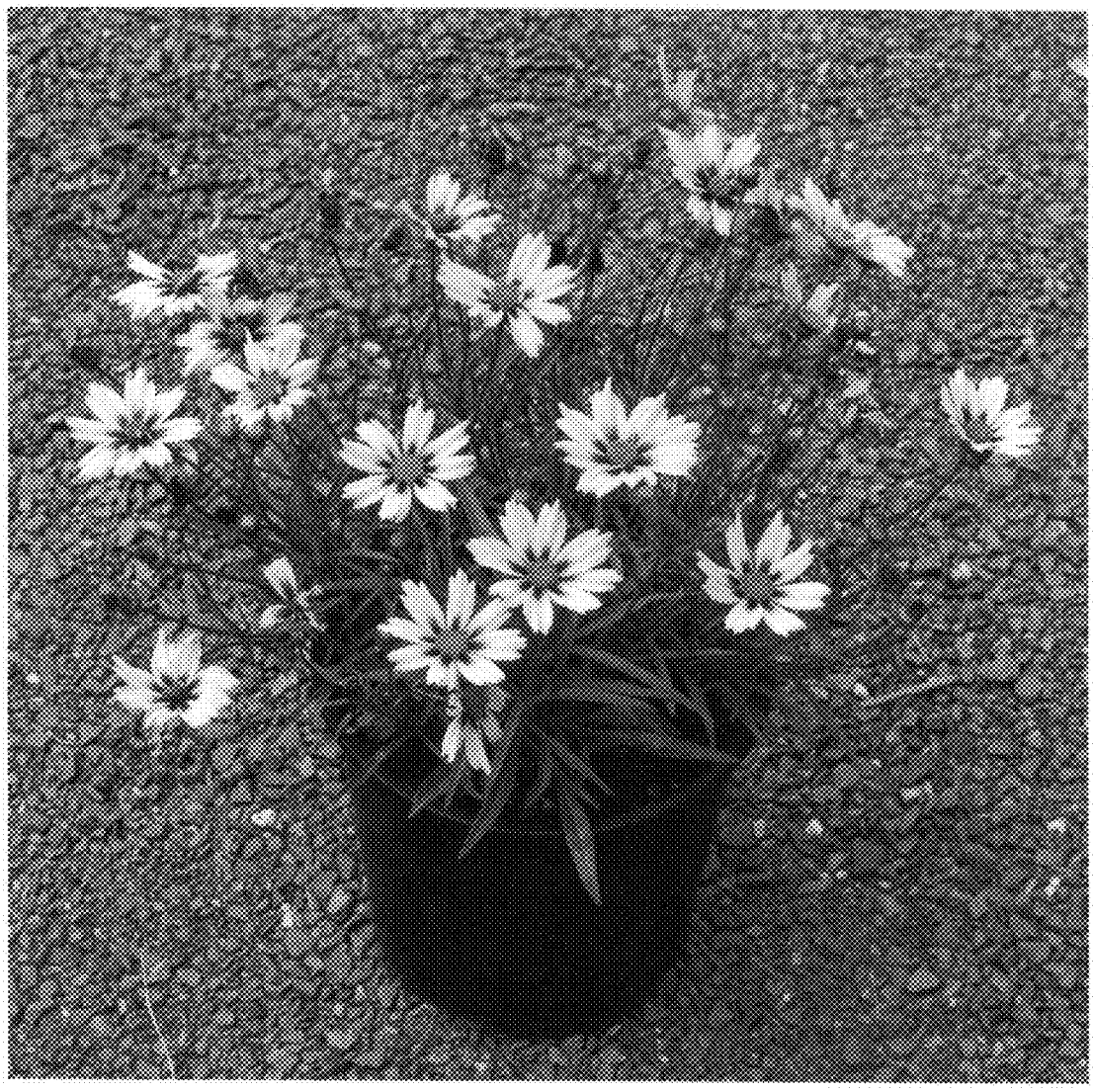
Figure 2:
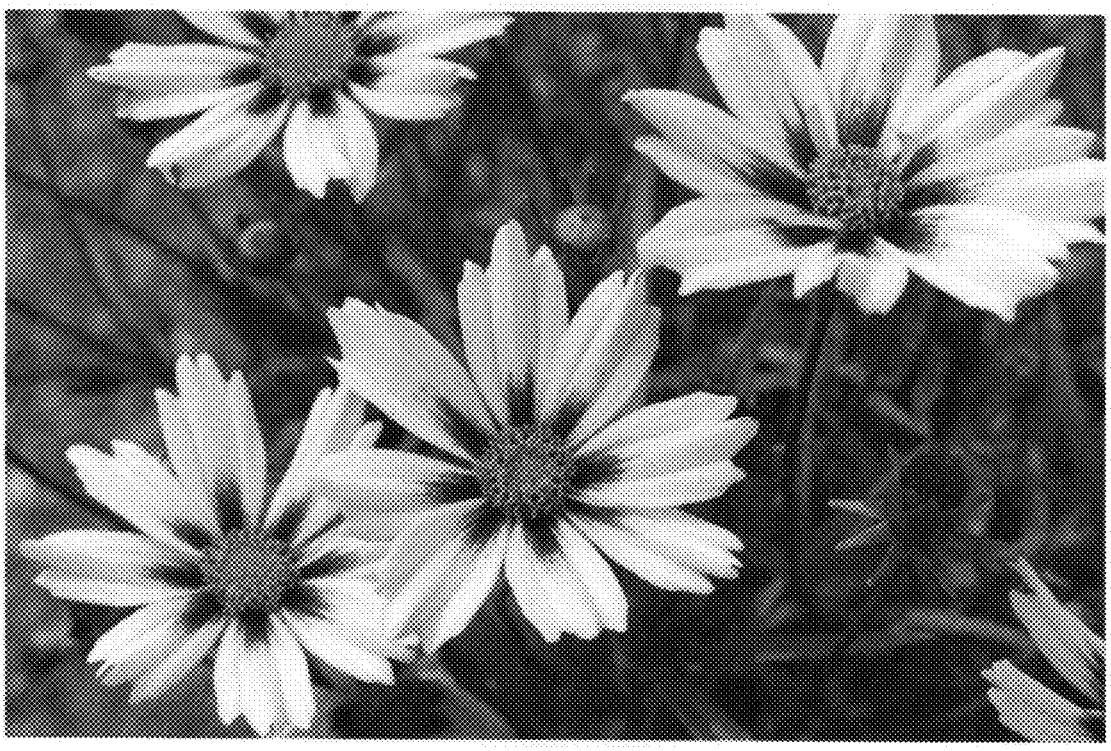

The photograph in FIG. 2 provides a close-up view of the inflorescences of 'Starlight' in warm temperatures.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of plants of the new cultivar three months in age as grown outdoors in one-gallon containers from a 128-cell plug in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from mid-June until hard frost in Kensington, Conn.

*Plant type*.—Herbaceous perennial.

*Plant habit*.—Compact, clump-forming, densely branched above ground with stems that spread outward.

*Height and spread*.—An average of 25 cm in height and 50 cm in width.

*Cold hardiness*.—At least in U.S.D.A Zone 5a.

*Diseases resistance*.—Has been observed to be highly resistant to powdery mildew caused by *Podosphaera macularis* and leaf spot caused by *Pseudomonas cichorii*.

*Root description*.—Fibrous when young, becoming more fleshy with age.

*Propagation*.—Stem cuttings.

*Growth rate*.—Vigorous.

Stem description:

*Shape*.—Round, solid.

*Stem color*.—Young and mature; 144A.

*Stem size*.—Main stem (excluding peduncles) average of 10 cm in length and 3 mm in width, lateral branches up to 5 cm in length (excluding peduncles) and 2 mm in width, secondary branches up to 3 cm in length and 2 mm in width.

*Stem surface*.—Young; glabrous, mature; ridged, dull and moderately covered with stiff pubescence average of 1 mm in length and ranges between being translucent and NN155D in color.

*Branching habit*.—An average of 4 main branches, each main branch has 3 to 4 lateral.

*Internode length*.—Variable, an average of 2 cm.

Foliage description:

*Leaf division*.—Simple.

*Leaf margins*.—Entire with slight undulations.

*Leaf size*.—Up to 5.5 cm in length and 5 mm in width.

*Leaf shape*.—Lanceolate.

*Leaf base*.—Attenuate.

*Leaf apex*.—Narrowly acute.

*Leaf venation*.—Pinnate, inconspicuous, coloration same as leaf on both surfaces.

*Leaf attachment*.—Sessile.

*Leaf arrangement*.—Opposite.

*Leaf surface*.—Young and mature upper and lower surfaces are dull and sparsely covered with a mix of stiff and soft pubescence average of 1 mm in length and ranges between being translucent and NN155D in color.

*Leaf color*.—Young and mature upper surface; 146A, young and mature lower surface; 146B.

Flower description:

*Inflorescence type*.—Composite with ray florets surrounding disk florets in the center, forming a radiant head, inflorescences are borne on terminals arising from leaf axils.

*Lastingness of inflorescence*.—About 10 days until senescence of ray florets, bracts and disk florets are persistent.

*Fragrance*.—Light fragrance.

*Quantity of inflorescences*.—An average of 5 per lateral branch, blooms are continuously produced until frost.

*Inflorescence size*.—Up to 1.3 cm in depth and 8 cm in diameter with disk portion up to 1 cm in diameter, first flowers on stem to open are the largest.

*Inflorescence buds*.—An average of 3 mm in depth and 5 mm in diameter, shape is spherical, color is 144A.

*Peduncles*.—Strong, an average of 4 to 11 cm in length and 2 mm in diameter, 146A in color, surface is dull and very sparsely covered with soft pubescence average of 1 mm in length and ranges between being translucent and NN155D in color.

Involucral bracts:

*Bract number*.—One row of 8.

*Bract arrangement*.—30% fused and somewhat reflexed when flower is fully open and becoming horizontal after ray florets drop.

*Bract size*.—Up to 1 cm in length and 3 mm in width.

*Bract color*.—Translucent, both surfaces 144A with outer edges N144A.

*Bract texture*.—Both surfaces glabrous.
*Bract apex*.—Acute.
*Bract base*.—Truncate.
*Bract margins*.—Entire.
*Bract shape*.—Lanceolate.

Ray florets (pistillate):
*Number*.—8.
*Shape*.—Oblanceolate, appearance of three longitudinal sections with center section longer, very slightly overlapping and apex of each free.
*Size*.—An average of 3 cm in length and 1.4 cm in width.
*Apex*.—3-lobed with center lobe bluntly acute, emarginate and side lobes bluntly acute.
*Base*.—Cuneate.
*Margins*.—Entire on sides, lobed at apex.
*Aspect*.—Held slightly upward and curved.
*Texture*.—Both surfaces glabrous.
*Color*.—When opening upper surface; a blend of 4C with slight overlays of 4B and 3A at the base and edges, 187B in the center near base, when opening lower surface; 4A, when fully open upper surface; a blend of 155A and 4C with slight overlays of 4B and 3A on the base edges and middle lobe, and a blend of 187A and 187B in the center near base and extending to the middle of the floret (degree of purple coloration is increased when grown under cooler temperatures), when fully open lower surface; a blend of 3C and 3A.

Disk florets (perfect):
*Number*.—An average of 100.
*Shape*.—Tubular, corolla is fused, flared at apex.
*Size*.—About 6 mm in length and 1 mm in width.
*Color*.—En masse; 14A, corolla; base (tube) is 12B in color and translucent, flared portion is 13A.
*Petaloids*.—Present occasionally, an average of 2, located near the disk floret outer ring, oblanceolate in shape, an average of 9 mm in length and 2 mm in width, 10A in color.
*Receptacle*.—About 8 mm in diameter and 4 mm in depth, 145C in color.

Reproductive organs:
*Presence*.—Disk florets are perfect, ray florets are pistillate.
*Gynoecium*.—1 Pistil, 5 mm in length, style is very fine and about 154CA in color and translucent, stigma is bifid, pilose, 14A in color with branches about 1 mm in length and recurved, ovary is 2 mm in length, 1 mm in width, inferior, and 11A in color.
*Androcoecium*.—5 stamens, fused into tube surrounding style, 1 mm in length and 0.5 mm in width, blend of 200A and N199C in color, no pollen was observed.
*Fruit/seed*.—No fruit or seed development was observed, plants have been observed to be nearly sterile.

It is claimed:

1. A new and distinct cultivar of *Coreopsis* plant named 'Starlight' as herein illustrated and described.

* * * * *